United States Patent [19]

Junge et al.

[11] 4,407,809

[45] Oct. 4, 1983

[54] N-PHENOXY(OR THIO)HYDROCARBON 3,4,5-TRIHYDROXYPIPERIDINE DERIVATIVES, THEIR USE IN MEDICINE AND IN ANIMAL NUTRITION

[75] Inventors: Bodo Junge, Wuppertal; Jürgen Stoltefuss, Haan; Lutz Müller, Wuppertal; Hans-Peter Krause, Wuppertal; Rüdiger Sitt, Wuppertal, all of Fed. Rep. of Germany

[73] Assignee: Bayer Aktiengesellschaft, Leverkusen, Fed. Rep. of Germany

[21] Appl. No.: 231,695

[22] Filed: Feb. 5, 1981

[30] Foreign Application Priority Data

Feb. 26, 1980 [DE] Fed. Rep. of Germany ....... 3007078

[51] Int. Cl.³ .................. A61K 31/445; C07D 211/40
[52] U.S. Cl. .................................... 424/267; 546/219; 546/220; 546/208; 542/413
[58] Field of Search ...................... 546/219, 220, 208; 542/413; 424/267

[56] References Cited

U.S. PATENT DOCUMENTS

| 4,182,767 | 1/1980 | Murai et al. | 424/267 |
| 4,260,622 | 4/1981 | Junge et al. | 546/219 |
| 4,278,683 | 7/1981 | Stoltefuss | 546/219 |

*Primary Examiner*—Jane T. Fan
*Attorney, Agent, or Firm*—Sprung, Horn, Kramer & Woods

[57] ABSTRACT

The invention relates to 3,4,5-trihydroxypiperidine compound of Formula (I) as methods for the preparation of said compounds. Also included in the invention are compositions containing said piperidine compounds and methods for the use of said piperidine compounds and compositions. The invention further includes veterinary compositions containing said piperidine compounds and their use in animal nutrition.

The piperidine compounds of Formula (I) are useful as agents against prediabetes, gastritis, constipation, infections of the gastro-intestinal tract, meteorism, flatulence, caries, arteriosclerosis and hypertension and in particular against diabetes, hyperlipaemia and adiposity, and also in animal nutrition for influencing the meat/fat ratio in favor of the meat content.

31 Claims, No Drawings

N-PHENOXY(OR THIO)HYDROCARBON 3,4,5-TRIHYDROXYPIPERIDINE DERIVATIVES, THEIR USE IN MEDICINE AND IN ANIMAL NUTRITION

The present invention relates to certain new 3,4,5-trihydroxypiperidine compounds, to processes for their production and to their use as agents against prediabetes, gastritis, constipation, infections of the gastro-intestinal tract, meteorism, flatulence, caries, arteriosclerosis and hypertension and in particular against diabetes, hyperlipaemia and adiposity, and also in animal nutrition for influencing the meat/fat ratio in favour of the meat content.

According to the present invention there are provided compounds which are 3,4,5-trihydroxypiperidine derivatives of the general formula

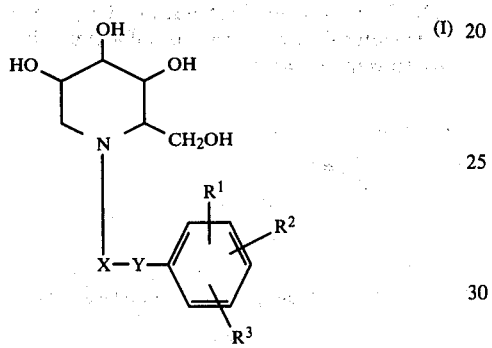

wherein
X represents a straight-chain or branched saturated or unsaturated hydrocarbon radical,
Y denotes oxygen or sulphur and
$R^1$, $R^2$ and $R^3$ are identical or different and independently of one another denote a hydrogen or halogen atom, an alkyl, aryl, alkoxy, aroxy, alkylthio, nitro, amino, hydroxyl, cyano, alkyl- and di-alkyl-amino, aminoalkyl, hydroxyalkyl, acylamino, sulfonylamino, acyloxy, carboxyl, carbalkoxy, alkylcarbonyl or formyl radical or an optionally substituted carbonamide or sulphonamide radical.

The invention preferentially relates to compounds of the formula (I) in which X denotes a saturated or mono-, di- or poly-unsaturated alkyl radical with 1 to 10 and preferably 2 to 5 carbon atoms and Y, $R^1$, $R^2$ and $R^3$ have the meaning indicated above. $R^1$, $R^2$ and $R^3$ preferably independently denote a hydrogen atom, an alkyl or alkoxy group, a halogen atom or a carboxyl, carbalkoxy, amino, acylamino, aryl or aminoalkyl group.

As used herein and unless otherwise specified, the term "halogen" preferably refers to chlorine, bromine or fluorine. The terms "alkyl", "alkoxy", "alkylthio", "alkyl-amino", "aminoalkyl", "hydroxyalkyl", "carbalkoxy" and "alkylcarbonyl" preferably refer to such groups having up to 12, particularly up to 8 carbon atoms; and the term "dialkyl-amino" preferably refers to such groups having up to 12, particularly up to 8 carbon atoms in each alkyl group. The terms "aryl" and "aroxy" preferably refer to mono- or bi-cyclic carbocyclic aryl or aryloxy, such as phenyl, phenoxy, biphenyl, bi-phenyloxy, naphthyl and naphthyl oxy. The term "acylamino" preferably refers to carboxylic acid or sulfonic acid acylamino, especially $C_1$-$C_7$ alkanoylamino. The term "acyloxy" preferably refers to carboxylic acid acyloxy, especially $C_1$-$C_7$ alkanoyloxy.

The term carboxamid preferably refers to a group —CO—$NR^4R^5$, in which $R^4$ and $R^5$ are identical or different and independently of one another denote hydrogen or $C_1$-$C_7$ alkyl, an optionally substituted phenyl, or $R^4$ and $R^5$ together give a heterocyclic ring.

It has been found that the new compounds of the present invention are potent inhibitors for α-glucosidases, especially for disaccharidases. The new compounds are therefore valuable agents for influencing a multiplicity of metabolic processes and are thus an enrichment of pharmacy.

According to the present invention there are further provided processes for the production of a compound of the present invention, in which (a) a compound of the formula

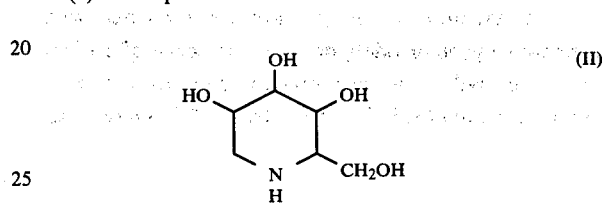

is reacted with an alkylating agent of the formula

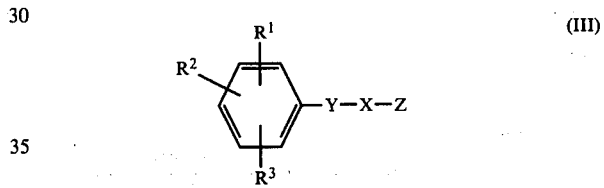

wherein
Z denotes an alkylating agent-functional group, for example a halogen atom or a sulphonic acid ester group, and
$R^1$, $R^2$, $R^3$, Y and X have the meanings indicated above, or (b) a compound of the formula (II), as defined above, is subjected to reductive alkylation with an aldehyde of the formula

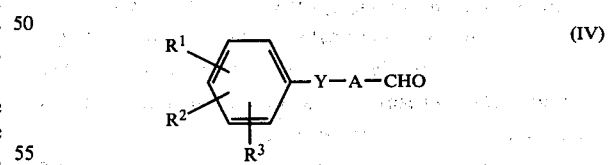

wherein
A represents a saturated or mono-, di- or polyunsaturated aliphatic radical which has one less carbon atoms than the deisred radical X, and
$R^1$, $R^2$, $R^3$ and Y have the meanings indicated above,
in the presence of a hydrogen donor.

If, for example, 1-desoxynojirimicin and 2-phenoxyethyl bromide are reacted together, the course of the reaction variant (a) is illustrated by the following equation:

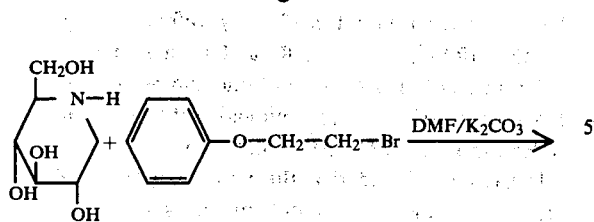

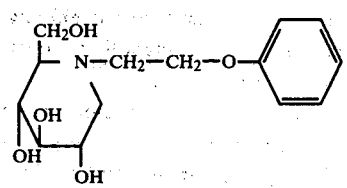

If, for example, 1-desoxynojirimicin is reacted with β-phenoxy-propionaldehyde in the presence of sodium cyanoborohydride as the hydrogen donor, the course of reaction variant (b) is illustrated by the following equation:

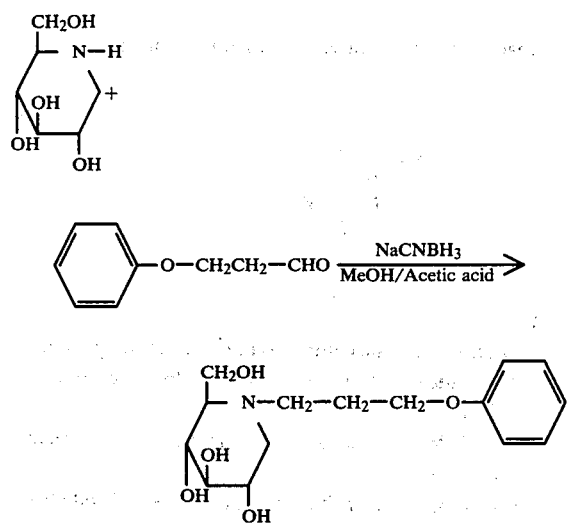

Furthermore compounds of formula I can be obtained by modifying functional groups in compounds of formula I by common chemical procedures. For example a compound of formula I in which $R^1$ denotes carboxy can be easily transformed into a compound of formula I in which $R^1$ denotes carboxamide.

The majority of the starting materials used are known or can be prepared by known processes. Thus, 1-desoxynojirimicin has been disclosed, for example, in European Published Patent Specification No. 947.

The alkylating agents of formula III are known or can be prepared by methods known from the literature. For example, if Z in formula III denotes bromine these compounds can be prepared by reacting an excess of a dibromide of the formula Br—X—Br, in which X has the meaning indicated above, with the sodium or potassium salt of the formula

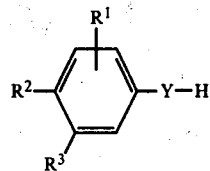

in an appropriate solvent. Suitable solvents are for example ether, alcohols like methanol and ethanol, water, THF and so on. The reaction temperature is usually identical with the boiling point of the solvent. Further details to prepare these alkylating agents can be taken from the following papers: (1.) A. Lüttringhaus, G. v. Sääf and K. Hauschild, Ber. 71, 1677 (1938); (2.) H. W. Bentley, E. H. Haworth and W. H. Perkin jun., J. Chem. Soc. 69, 161 (1896); (3.) "Organic Syntheses" 9,72 (1929). For the preparation of 1-phenoxy-4-bromo-trans-buten-2 this procedure is illustrated by the following formula scheme.

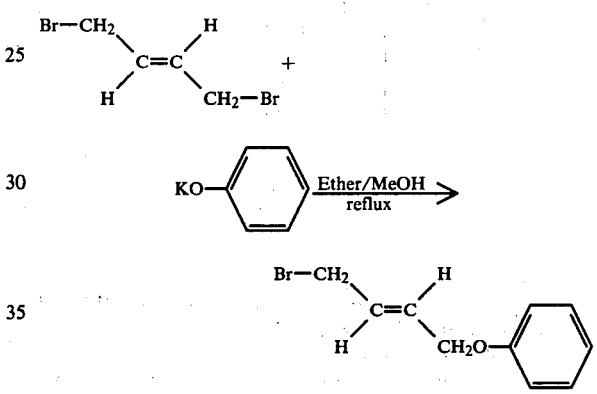

For the preparation of 4-(2-bromo-ethoxy)-ethyl-benzoate this procedure is illustrated by the following formula scheme.

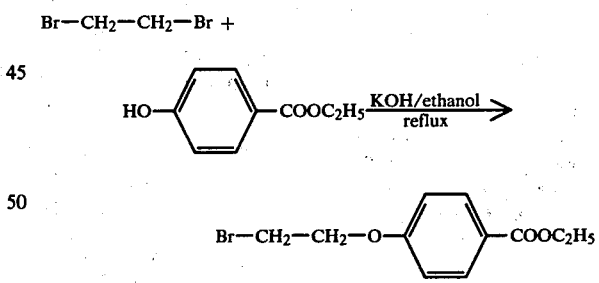

The reaction variant (a) is generally carried out in a polar, protic or aprotic solvent, appropriately in the presence of an acid-binding agent at a temperature between 0° C. and the boiling point of the solvent. The reaction is preferably carried out in DMF in the presence of potassium carbonate or triethylamine.

The hydrogen donor used for the reductive alkylation of reaction variant (b) can be catalytically activated hydrogen. The catalyst used is in particular Raney nickel, but noble metal catalysts can also be used. The reaction is in general carried out under a pressure of between 1 and 150 atmospheres $H_2$ pressure and at a temperature between 20° and 150° C. Preferred solvents are protic, polar solvents, especially alcohols.

Alkali metal (particularly sodium or potassium) cyanoborohydrides, dialkylaminoboranes (particularly $C_1$–$C_4$-alkylaminoboranes) and alkali metal (particularly sodium or potassium) borohydrides can also be used as hydrogen donor/reducing agents. The use of sodium cyanoborohydride is particularly preferred in this process varient. The reaction is in general carried out at room temperature. However, it can also be advantageous to heat to the reflux temperature.

The process is customarily carried out in a solvent which is inert under the reaction conditions. Although anhydrous aprotic solvents can be employed (for example tetrahydrofurane, if the reducing agent is morpholinoborane), a protic solvent is, nevertheless, customarily used. A suitable protic solvent is in particular a $C_1$–$C_4$ alkanol. However, water or an aqueous $C_1$–$C_4$ alkanol (for example aqueous methanol or ethanol) or other aqueous solvent systems, such as aqueous dimethylformamide, aqueous hexamethylphosphoric acid triamide, aqueous tetrahydrofurane or aqueous ethylene glycol dimethyl ether, can also be used.

The process is usually carried out in a pH range of 1 to 11, and a pH range between 4 and 7 is preferred.

The compounds according to the present invention (hereinafter alternatively referred to as "inhibitors according to the invention") are suitable as therapeutic agents for the following indications:

Prediabetes, gastritis, constipation, infections of the gastro-intestinal tract, meteorism, flatulence, caries, arteriosclerosis, hypertension and, in particular, adiposity, diabetes and hyperlipoproteinaemia.

To broaden the action spectrum, it can be advisable to combine inhibitors for glycoside hydrolases which complement one another in their action, the combinations being either combinations of the inhibitors according to the invention with one another or combinations of the inhibitors according to the invention with inhibitors which are already known. Thus, for example, it can be appropriate to combine saccharase inhibitors according to the invention with amylase inhibitors which are already known.

In some cases, combinations of the inhibitors according to the invention with known oral antidiabetic agents ($\beta$-cytotropic sulphenylurea derivatives and/or biguanides having an action on the blood sugar), with active compounds which lower the blood lipid level, such as clofibrate, nicotinic acid, cholestyramine and others, are also advantageous.

As stated above, the invention also relates to the use in medicine of the compounds of the invention.

The present invention provides a pharmaceutical composition containing as active ingredient a compound of the invention in admixute with an inert pharmaceutical carrier, such as a solid or liquefied gaseous diluent, or a liquid diluent other than a solvent of a molecular weight less than 200 (preferably less than 350) except in the presence of a surface active agent.

The invention also provides a medicament in dosage unit form comprising a compound of the invention.

The invention also provides a medicament in the form of tablets (including lozenges and granules), dragees, capsules, pills, or ampoules comprising a compound of the invention. "Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of suspensions, solutions and emulsions of the active ingredient in aqueous or non-aqueous diluents, syrups, granulates or powders.

The pharmaceutical compositions according to the invention generally contain from 0.1 to 99.5% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, and ampoules. Some of these forms may be made up for delayed release of the active ingredient. Some, such as capsules, include a protective envelope which renders the portions of the medicament physically discrete and coherent.

This invention further provides a method combating the above-mentioned diseases in warm-blooded animals, which comprises administering to the animals a compound of the invention alone or in admixture with a diluent or in the form of a medicament according to the invention.

In general it has proved advantageous to administer amounts of from 1 to $1 \times 10^4$ saccharase inhibitor units kg of body weight per day to achieve effective results. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered .Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

A powder is prepared by comminuting the substance to a suitable size and mixing it with a pharmaceutical excipient, which is likewise comminuted. Although an edible carbohydrate, such as starch, lactose, sucrose or glucose is usally used for this purpose and can also be used in this case, it is desirable to use a carbohydrate which cannot be metabolised, for example, a cellulose derivative.

Sweeteners, flavouring additives, preservatives, dispersing agents and colouring agents can also be co-used.

The capsules can be produced by preparing the powder mixture described above and by filling gelating casing which have already been formed. Before the filling operation, lubricants, such as, for example, silica gel, talc, magnesium stearate, calcium stearate or solid polyethylene glycol, can be added to the powder mixture. A disintegrator or solubilising agent for example agar-agar, calcium carbonate or sodium carbonate, can likewise be added to the mixture in order to improve the accessibility of the inhibitor when the capsule is taken.

Tablets are produced, for example, by preparing a powder mixture, of coarse or fine grain size, and adding a lubricant and disintegrator. Tablets are formed from this mixture. A powder mixture is prepared by mixing the substance, which has been comminuted in a suitable manner, and making up with a diluent or another excipient, as described above. Further substances which are added if appropriate are a binder: for example carboxymethylcellulose, alginates, gelatine or polyvinylpyrrolidones, a solution retarder, for example paraffin, a resorption accelerator, for example a quaternary salt, and/or an adsorbent, for example, bentonite, kaolin or dicalcium phosphate. The powder mixture can be granulated, together with a binder, for example syrup, starch paste or acacia mucillage, or solutions of cellulose materials or polymeric materials. The product is then pressed through a coarse sieve. As an alternative to this, the powder mixture can be allowed to run through a tabletting machine and the resulting pieces of non-uniform shape can be comminuted down to a particle size. A lubricant, for example stearic acid, a stearate salt, talc or mineral oil, can be added to the resulting particles so that these do not stick in the tablet-forming nozzles. This mixture, which has been given slip properties, is then pressed into tablet form. The active compounds can also be combined with free-flowing inert excipients and brought direct into tablet form omitting the granulating or fragmentation steps. The product can be provided with a clear or opaque protective shell, for example a coating of shellac, a coating of sugar or polymeric substances and a polished shell of wax. Dyestuffs can be added to these coatings so that the different dosage units can be differentiated.

The formulation forms to be administered orally, for example, solutions, syrup and elixirs, can be prepared in dosage units, so that a specific amount of the formulation contains a specific amount of active compound. A syrup can be prepared by dissolving the active compound in an aqueous solution which contains suitable flavouring agents; elixirs are obtained using non-toxic, alcoholic excipients. Suspensions can be prepared by dispersing the compound in a non-toxic excipient. Solubilising agents and emulsifying agents, for example ethoxylated isostearyl alcohols and polyoxyethylenesorbitol esters, preservatives, flavour-improving additives, for example peppermint oil or saccharin can also be added.

Dosage instructions can be indicated on the capsule. In addition, it is possible to safeguard the dosage by releasing the active compound in a delayed manner, for example by enclosing the active compound in polymer substances, waxes or the like.

In addition to the abovementioned pharmaceutical compositions, foodstuffs containing these active compounds can also be prepared; for example sugar, bread, potato products, fruit juice, beer, chocolate and other confectionery, and preserves, for example jam, and in this case a therapeutically effective amount of at least one on the inhibitors according to the invention is added to these products.

The foodstuffs produced using the active compounds according to the invention are suitable both for the diet of patients suffering from metabolism disorders and for the nutrition of healthy persons in the sense of a diet which prevents metabolism disorders.

The inhibitors according to the invention furthermore have the property of influencing to a greater extent of the relationship between the proportion of undesired fat to the proportion of desired meat of low fat content (lean meat) in animals in favour of the lean meat. This is of particular importance for rearing and keeping agricultural livestock, for example in the fattening of pigs, but is also of considerable importance for rearing and keeping other livestock and pets. Using the inhibitors can furthermore lead to a considerable rationalisation of feeding of animals, from the point of view of time, quantity and quality. Since the inhibitors cause a certain delay in digestion, the residence time of the nutrients in the digestive tract is extended and this makes possible ad libitum feeding, which is associated with a low expenditure. Moreover, using the inhibitors according to the invention in many cases results in a considerable saving of valuable protein feed.

The active compounds can thus be used in virtually all fields of animal nutrition as agents for reducing the deposition of fat and for saving feed protein.

The activity of the active compounds is largely independent of the species and sex of the animals. The active compounds prove particularly valuable in the case of species of animals which, generally or at certain periods of their life, tend to deposit relatively large amounts of fat.

The following livestock and pets may be mentioned as examples of animals for which the inhibitors can be employed for reducing the deposition of fat and/or for saving feed protein: warm-blooded animals, such as cattle, pigs, horses, sheep, goats, cats, dogs, rabbits, fur-bearing animals, for example mink and chinchillas, other pets, for example guineapigs and hamsters, laboratory animals and zoo animals, for example rats, mice and apes, and poultry, for example broilers, hens, geese, ducks, turkeys, pigeons, parrots and canaries, and cold-blooded animals, such as fish, for example carp, and reptiles, for example snakes.

Because of the favourable properties of the active compounds, the amount of the active compounds which is administered to the animals to achieve the desired effect can be varied substantially. It is preferably about 0.1 mg to 1.0 g and in particular 1 to 100 mg/kg of feed per day. The period of administration can be from a few hours or days up to several years. The appropriate amount of active compound and the appropriate period of administration are closely related to the aim of feeding. They depend, in particular, on the species, age, sex, state of health and nature of keeping of the animals and can easily be determined by any expert.

The active compounds according to the invention are administered to the animals by the customary methods. The nature of the administration depends, in particular, on the species, the behaviour and the general condition of the animals. Thus, administration can be effected orally once or several times daily at regular or irregular intervals. For reasons of expediency, in most cases oral administration, in particular in the rythm of the intake of food and/or drink by the animals, is to be preferred.

The active compounds can be administered as pure substances or in the formulated form, the formulated form being understood as a premix, that is to say as a mixture with non-toxic inert carriers of any desired nature, as a part of a total ration in the form of a supplementary feed or as a mixing component of a mixed feed for use by itself. Administration of suitable formulations via the drinking water is also included.

The active compounds, optionally in the formulated form, can also be administered in a suitable form together with other nutrients and active compounds, for example mineral salts, trace elements, vitamins, proteins, energy carriers (for example starch, sugars, fats), dyestuffs and/or flavouring agents or other feed additives, such as growth promoters. The active compounds can be administered to the animals before, during or after intake of the feed.

Oral administration together with the feed and/or drinking water is recommended, the active compounds being added to all or only parts of the feed and/or drinking water as required.

The active compounds can be admixed to the feed and/or drinking water in accordance with customary methods by simple mixing as pure substances, preferably in the finely divided form or in the formulated form mixed with edible, non-toxic carriers, and optionally also in the form of a premix or a feed concentrate.

According to the present invention we thus further provide a medicated feed comprising an active compound of the present invention in admixture with a nutritious material.

The feed and/or drinking water can contain the active compounds according to the invention in a concentration of, for example, about 0.001 to 5.0%, in particular 0.02 to 2.0% (by weight). The optimum level of the concentration of the active compound in the feed and/or drinking water depends, in particular, on the amount of feed and/or drinking water taken in by the animals and can easily be determined by any expert.

The nature of the feed and its composition is irrelevant in this context. All the customary commercially available or specific feed compositions, which preferably contain the customary equilibrium of energy substances and proteins, including vitamins and mineral substances, necessary for balances nutrition, can be used. The feed can be composed, for example, of vegetable substances, for example shredded oilcake, shredded cereal and cereal by-products, and also hay, silage fodder, beet and other forage plants, of animal substances, for example meat products and fish products, bone meal, fats, vitamins, for example A, D, E, K and B complex, and specific sources of protein, for example yeasts, and certain aminoacids and mineral substances and trace elements, such as, for example, phosphorus and iron, zinc, manganese, copper, cobalt, iodine and the like.

Premixes can preferably contain from 0.1 to 50%, in particular 0.5 to 5.0% (by weight) of an active compound according to the invention, in addition to any desired edible carriers and/or mineral salts, for example carbonated feed lime, and are prepared by the customary mixing methods.

Mixed feed preferably contain 0.001 to 5.0%, in particular 0.02 to 2.0% (by weight) of an active compound according to the invention, in addition to the customary raw material components of a mixed feed, for example shredded cereal or cereal by-products, shredded oilcake, animal protein, minerals, trace elements and vitamins. They can be prepared by the customary mixing methods.

In premixes and mixed feedstuffs, preferably, the active compounds can also optionally be protected from air, light, and/or moisture by suitable agents which coat their surface, for example with non-toxic waxes or gelatine.

The following is an example of the composition of a finished mixed feed for poultry, which contains an active compound according to the invention: 200 g of wheat, 340 g of maize, 360.3 g of coarse soya bean meal, 60 g of beef tallow, 15 g of dicalcium phosphate, 10 g of calcium carbonate, 4 g of iodonated sodium chloride, 7.5 g of a vitamin/mineral mixture and 3.2 g of an active compound premix give, after careful mixing, 1 kg of feed.

A vitamin/mineral mixture can consist of, for example: 6,000 I.U. of vitamin A, 1,000 I.U. of vitamin $D_3$, 10 mg of vitamin E, 1 mg of vitamin $K_3$, 3 mg of riboflavin, 2 mg of pyridoxine, 20 mg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7H_2O$, 100 mg of $FeSO_4 \times 7H_2O$ and 20 mg of $CuSO_4 \times 5H_2O$.

The active compound premix contains an active compound according to the invention in the desired amount, for example 1,600 mg, and in addition 1 g of DL-methionine as well as an amount of soya bean meal such that 3.2 g of premix are formed.

The following is an example of a composition of a mixed feed for pigs, which contains an active compound of the formula (I): 630 g of shredded cereal feed (composed of 200 g of shredded maize, 150 g of shredded barley, 150 g of shredded oats and 130 g of shredded wheat), 80 g of fish meal, 60 g of coarse soya bean meal, 58.8 g of tapioca meal, 38 g of brewer's yeast, 50 g of a vitamin/mineral mixture for pigs (composition, for example, as for the chick feed), 30 g of linseed cake meal, 30 g of maize gluten feed, 10 g of soya bean oil, 10 g of sugarcane molasses and 2 g of an active compound premix (composition, for example, as for the chick feed) give, after careful mixing, 1 kg of feed.

The feed mixtures indicated are intended preferably for rearing and fattening chicks or pigs respectively, but they can also be used, in the same or a similar composition, for rearing and fattening other animals.

The inhibitors can be used individually or in any desired mixtures with one another.

In vitro saccharase inhibition test The in vitro saccharase inhibition test makes it possible to determine the inhibitory activity of a substance on enzymes by comparing the activity of solubilised intestinal disaccharidase complex in the presence and in the absence (so-called 100% value) of the inhibitor. A virtually glucose-free sucrose (glucose < 100 ppm) is used as the substrate which determines the specificity of the inhibition test; the determination of the enzyme activity is based on the spectrophotometric determination of glucose liberated by means of glucose dehydrogenase and nicotinamide-adenine dinucleotide as the cofactor.

A saccharase inhibitor unit (SIU) is defined as the inhibitory activity which reduces a given saccharolytic activity in a defined test batch by one unit (saccharase unit=SU); the saccharase unit is thereby defined as the enzyme activity which, under the given conditions, splits one μmol of sucrose per minute and thus leads to the liberation of one μmol each of glucose, which is determined in the test, and fructose, which is not recorded in the test.

The intestinal disaccharidase complex is obtained from swine small intestine mucosa by tryptic digestion, precipitation from 66% strength ethanol at −20° C., taking up of the precipitate in 100 mM phosphate buffer of pH 7.0 and finally dialysis against the same buffer.

100 μl of a dilution of the intestinal disaccharidase complex in 0.1 M maleate buffer of pH 6.25 are added to 10 μl of a sample solution which is made up such that the extinction of the test batch is at least 10%, but not more than 25%, below that of the 100% value, and the mixture is pre-incubated at 37° C. for 10 minutes. The dilution of the disaccharidase complex is to be adjusted to an activity of 0.1 SU/ml.

The saccharolytic reaction is then started by adding 100 μl of a 0.4 M solution of sucrose ("SERVA 35579") in 0.1 M maleate buffer of pH 6.25 and, after an incubation period of 20 minutes at 37° C., is stopped by adding 1 ml of glucose dehydrogenase reagent (1 small bottle of a lyophilised glucose dehydrogenase/mutarotase mixture ("MERCK 14053") and 331.7 mg of β-nicotinamide-adenine dinucleotide (free acid, "BOEHRINGER", degree of purity I) dissolved in 250 ml of 0.5 M tris buffer of pH 7.6). To determine the glucose, the mixture is incubated at 37° C. for 30 minutes and finally measured photometrically at 340 nm against a reagent blank (with the enzyme but without sucrose).

Calculation of the inhibitory activity of inhibitors is made difficult by the fact that even slight changes in the test system, for example a 100% value which varies slightly from determination to determination, have an influence on the test result which can no longer be ignored. These difficulties are by-passed by running a standard with each determination; a saccharase inhibitor of the formula $C_{25}H_{43}O_{18}N$ which has a specific inhibitory activity of 77,700 SIU/g and, when employed in the test in amounts of 10 to 20 ng, leads to an inhibition of the order of size specified above, is used as the standard. When the difference in the extinctions at 340 nm between the 100% value and the batch inhibited by the standard is known, it is possible to calculate the specific inhibitory activity of the inhibitor, expressed in saccharase inhibitor units per gram (SIU/g), in a known manner from the difference in extinction between 100% value and the batch inhibited by the sample solution, taking into consideration the amount of inhibitor employed.

The following Examples illustrate processes for the production of compounds of the present invention.

EXAMPLE 1

N-β-Phenoxyethyl-1-desoxynojirimicin

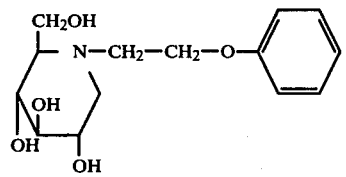

A suspension of 9.7 g of desoxynojirimicin and 12.4 g of powdered potassium carbonate in 100 ml of absolute dimethylformamide was stirred with 15.7 g of β-phenoxyethyl bromide for 5 hours at 90° to 100° C. It was cooled and filtered. The filtrate was concentrated in a rotary evaporator at a batch temperature of 60° C. The evaporation residue was dissolved in a little hot water, the solution was kept at 5° C. for 18 hours and the resulting crystals were filtered off and washed with ice-water. 10.5 g of a crystalline product with a melting point of 146° C. were obtained.

EXAMPLE 2

N-(5-Phenoxy-pentyl)-1-desoxynojirimicin

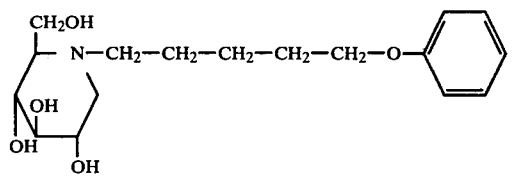

4.6 g of 1-desoxynojirimicin were stirred with 6.2 g of powdered potassium carbonate and 11 g of 5-phenoxypentyl bromide for 5 hours at 100° C. The mixture was cooled and filtered. The filtrate was concentrated in a rotary evaporator at 70° C. The resulting evaporation residue was dissolved in about 300 ml of ethanol. After adding Tensil as a filter aid, the solution was filtered and the filtrate was concentrated. The semi-solid product was stirred with acetonitrile, filtered off and washed with acetonitrile and water. 6.35 g of a colourless product with a melting point of 138° to 139° C. were obtained.

The following compounds were prepared analogously:

EXAMPLE 3

N-(4-Phenoxybutyl)-1-desoxynojirimicin with a melting point above 110° C.

EXAMPLE 4

N-[β-(2,6-Dimethyl-phenoxy)-ethyl]-1-desoxynojirimicin with a melting point of 155° to 56° C.

EXAMPLE 5

N-[γ-(2,6-Dimethoxyphenoxy)-propyl]-1-desoxynojirimicin with a melting point of 128° C.

EXAMPLE 6

N-[β-(2,4-Dichlorophenoxy)-ethyl]-1-desoxynojirimicin with a melting point of 175° to 76° C.

EXAMPLE 7

N-(γ-Phenoxypropyl)-1-desoxynojirimicin with a melting point of 152° C.

EXAMPLE 8

N-(4-Phenoxy-trans-buten-2-yl)-1-desoxynojirimicin hydrate

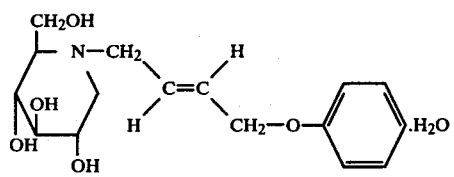

6.2 g of 1-phenoxy-4-bromo-trans-but-2-ene were added to a suspension of 3.6 g of 1-desoxynojirimicin and 4.55 g of ground potassium carbonate in 40 ml of absolute dimethylformamide and the mixture was stirred for 5 hours at 100° C. It was cooled and the salt was filtered off. The filtrate was concentrated at 60° and the evaporation residue was stirred with a little water. The resulting solid product was filtered off and washed with a little water and isopropanol. After recrystallisation from water, 3.1 g of virtually colourless crystals with a melting point of 120° C. were obtained.

The following compounds were prepared analogously:

EXAMPLE 9

N-(4-p-Methoxyphenyloxy-trans-buten-2-yl)-1-desoxynojirimicin

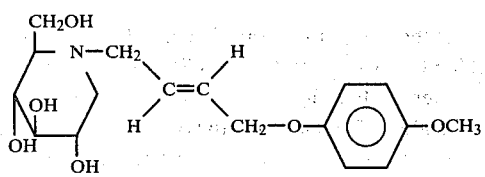

Melting point: 163° to 166° C.
Preparation of the starting material:
The starting material 1-p-methoxyphenyloxy-4-bromo-trans-but-2-ene was prepared from 1,4-dibromo-trans-but-2-ene and p-methoxyphenol by the method of A Lüttinghaus et al. (Ber. 71, 1677 (1938)). Melting point: 58° C.

EXAMPLE 10

N-[4-(4-Carbethoxyphenoxy)-buten-2-yl]-1-desoxynojirimicin

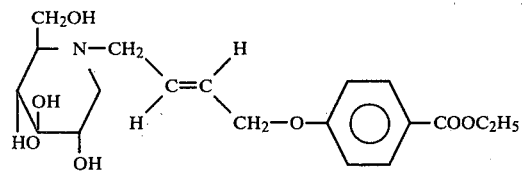

EXAMPLE 11

N-[β-(4-Methoxy-phenoxy)-ethyl]-1-desoxynojirimicin with a melting point of 175° to 78° C.

EXAMPLE 12

N-[β-(4-Chlorophenoxy)-ethyl]-1-desoxynojirimicin with a melting point of 156° to 57° C.

EXAMPLE 13

N-[β-(4-Cyano-phenoxy)-ethyl]-1-desoxynojirimicin with a melting point of 125° C.

EXAMPLE 14

N-[β-(3-Methylphenoxy)-ethyl]-1-desoxynojirimicin with a melting point of 132° to 34° C.

EXAMPLE 15

(a) Preparation of 2-Phenylthioethyl bromide
33 g of thiophenol were dissolved in a solution of 6.9 g of sodium in 120 ml of ethanol and the solution was added dropwise to 129 ml of 1,2-dibromoethane. The mixture was heated under reflux for 1 hour and cooled and 250 ml of ether were added. The salt which had precipitated out was filtered off. The filtrate was concentrated and the evaporation residue was fractionated. 55.4 g of a colourless oil with a boiling point of 125° to 130° C. under 12 mm Hg were obtained.

(b) N-(β-Phenylthioethyl)-1-desoxynojirimicin

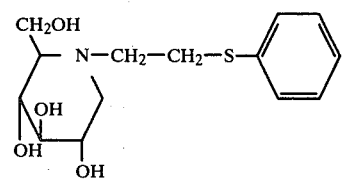

19.4 g of 1-desoxynojirimicin were stirred with 24.8 g of powdered potassium carbonate and 33.9 g of 2-phenylthioethyl bromide in 200 ml of absolute DMF for 8 hours at 90° to 100° C. The mixture was cooled and filtered and the filtrate was concentrated in a rotary evaporator at 60° C. The oily evaporation residue was purified through a 120 cm long and 6 cm wide column which contained cellulose as the stationary phase and first acetone and then 95% strength acetone as the mobile phase. The clean fractions were combined and concentrated. The product was recrystallised from isopropanol. This gave 16.3 g of a colourless substance with a melting point of 121° to 123° C.

The following compound was obtained analogously:

EXAMPLE 16

N-[β-(4-Methylphenylthio)-ethyl]-1-desoxynojirimicin with a melting point of 126° to 27° C.

EXAMPLE 17

(a) Preparation of 4-(3-methylphenylthio)-buten-2-yl bromide 14.9 g of 3-methylthiophenol were added to a solution of 2.76 g of sodium in 80 ml of absolute methanol and the mixture was then added dropwise at 30°–35° C. to a solution of 85.6 g of 1,4-dibromobut-2-ene in 100 ml of ether. The resulting mixture was heated at the boil for 30 minutes, cooled and filtered. The filtrate was concentrated in a rotary evaporator at a bath temperature of 30° C. and the evaporation residue was substantially freed from excess 1,4-dibromobut-2-ene at a bath temperature of 110° C. and 1 mm Hg. The resulting distillation residue, which weighed 22 g, was reacted without further purification.

(b) N-[4-(3-Methylphenylthio)-buten-2-yl]-1-desoxynojirimicin

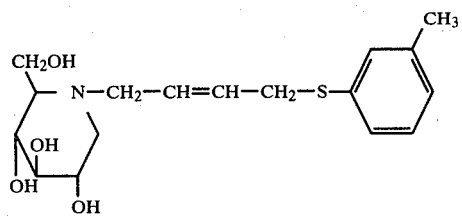

A mixture of 7.2 g of 1-desoxynojirimicin, 9.1 g of powdered potassium carbonate and 22 g of 4-(3-methylphenylthio)-buten-2-yl bromide in 80 ml of absolute DMF was stirred for 7 hours at 100° C. The mixture was cooled and filtered and the filtrate was concentrated. The resulting evaporation residue was introduced into a column which contained cellulose as the stationary phase and acetone as the mobile phase. The pure product was obtained using 95% acetone. The clean fractions were concentrated. The product was crystallised with a little ethanol. Colourless crystals with a melting point of 106° C. were obtained.

EXAMPLE 18

N-[4-(4-Chlorophenylthio)-buten-2-yl]-1-desoxynojirimicin

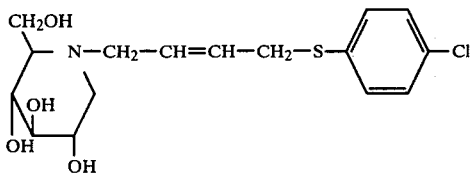

7.2 g of 1-desoxynojirimicin, 9.1 g of potassium carbonate and 20.8 g of 4-(4-chlorophenylthio)-buten-2-yl bromide (crude) were stirred in 80 ml of absolute DMF for 6 hours at 100° C. The mixture was cooled and filtered and the filtrate was concentrated. The evaporation residue was ground with water and the resulting solid product was filtered off. After recrystallisation from acetonitrile with a little isopropanol, 6.7 g of colourless crystals with a melting point of 93° to 95° C. were obtained.

The following compounds were prepared analogously:

EXAMPLE 19

N-[4-tert.-Butylphenylthio)-buten-2-yl]-1-desoxynojirimicin with a melting point of 138° to 40° C.

EXAMPLE 20

N-[4-(4-Methylphenylthio)-buten-2-yl]-1-desoxynojirimicin with a melting point above 83° C.

EXAMPLE 21

N-[4-(4-Phenylphenoxy)-buten-2-yl]-1-desoxynojirimicin with a melting point of 165° to 69° C.

The following compounds were prepared analogously to Example 1:

EXAMPLE 22

N-[β-(4-Acetamidophenoxy)-ethyl]-1-desoxynojirimicin with a melting point of 169° to 170° C.

EXAMPLE 23

N-[β-(4-Ethoxycarbonyl-phenoxy)-ethyl]-1-desoxynojirimicin with a melting point of 154° C.

EXAMPLE 24

N-[β-(4-Formylphenoxy)-ethyl]-1-desoxynojirimicin with a melting point of 149° C.

EXAMPLE 25

N-[β-(4-Hydroxyphenoxy)-ethyl]-1-desoxynojirimicin with a melting point of 149° to 151° C.

EXAMPLE 26

N-[β-(3-Ethoxycarbonylphenoxy)-ethyl]-1-desoxynojirimicin with a melting point of 116° C.

EXAMPLE 27

N-[4-(4-Acetamidophenoxy)-buten-2-yl]-1-desoxynojirimicin hydrate with a melting point of 82° C.

EXAMPLE 28

N-[β-(4-Aminomethylphenoxy)-ethyl]-1-desoxynojirmicin

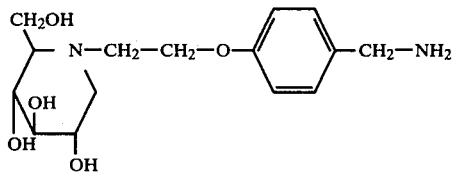

5 g of the compound from Example 13 were dissolved in 200 ml of water and 50 ml of 25% strength ammonia and, after adding Raney nickel, hydrogenated for 2 hours under 3.5 bars. The catalyst was filtered off, the filtrate was concentrated and the product was crystallised with methanol. This gave 3.0 g of colourless crystals with a melting point of 169° C.

EXAMPLE 29

N-[β-(4-Hydroxymethylphenoxy)-ethyl]-1-desoxynojirimicin with a melting point of 173° to 74° C. was obtained by hydrogenation of the compound from Example 24.

EXAMPLE 30

N-[4-(4-Aminophenoxy)-but-2-en-yl]-1-desoxynojirmicin

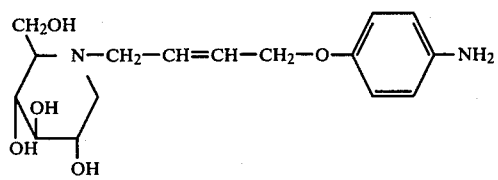

2.6 g of the compound from Example 27 were stirred with 11 ml of half-concentrated hydrochloric acid for 120 minutes at 80°–85° C., the mixture was concentrated and the product was purified by means of a cation exchanger. After recrystallisation from water, 400 mg of a colourless substance with a melting point of 110° C. were obtained.

EXAMPLE 31

N-[β-(4-Aminophenoxy)-ethyl]-1-desoxynojirimicin dihydrochloride with a melting point of 272° C. with decomposition was obtained by hydrochloric acid hydrolysis of the compound from Example 22.

EXAMPLE 32

N-[β-(4-Hydroxycarbonylphenoxy)-ethyl]-1-desoxynojirimicin

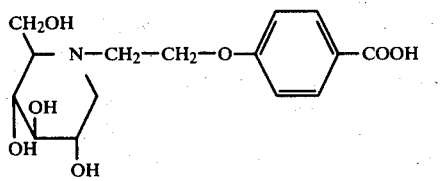

1 g of the compound from Example 23 was stirred in 10 ml of 1 N sodium hydroxide solution for 1 hour at 80° to 90° C. 10 ml of 1 N hydrochloric acid were added, the mixture was concentrated, the residue was stirred with a little water and the product was filtered off and washed with water. This gave 0.8 g of a colourless substance with a melting point of 235° to 37° C.

EXAMPLE 33

N-[β-(3-Hydroxycarbonylphenoxy)-ethyl]-1-desoxynojirimicin was obtained analogously to Example 32 by hydrolysis of the compound from Example 26 and was isolated in the form of a foam.

EXAMPLE 34

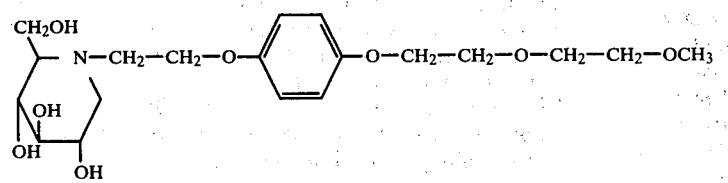

0.23 g of sodium were dissolved in 40 ml of absolute ethanol, and 3 g of the compound from Example 25 were added. The mixture was concentrated, and after adding DMF was concentrated again. The evaporation residue was dissolved in 10 ml of absolute DMF, 2.7 g of β-bromo-β'-methoxy-diethyl ether were added and the mixture was stirred for 4 hours at 100° C. to 120° C. The mixture was concentrated and the residue was purified through an acetone/cellulose column. After recrystallisation from acetone, 600 mg of virtually colourless crystals with a melting point of 118° C. were obtained.

EXAMPLE 35

N-[β-(4-tert.-Butylphenylthio)-ethyl]-1-desoxynojirimicin was obtained, in the form of a colourless oil, analogously to Example 15 from 1-desoxynojirimicin and β-(4-tert.-butylphenylthio)-ethyl bromide.

EXAMPLE 36

N-(4-Phenylthiobut-en-2-yl)-1-desoxynojirimicin with a melting point of 117° to 119° C. was prepared analogously to Example 17.

Example 37

N-[β-(4-Cyanomethylphenoxy)-ethyl]-1-desoxynojirimycin with a melting point of 128° to 132° C.

EXAMPLE 38

N-[β-(4-Aminoethylphenoxy)-ethyl]-1-desoxynojirimycin with a melting point of 159° to 162° C. was obtained by hydrogenation of Example No. 37 analogously to Example 38.

The present invention also comprises pharmaceutically acceptable bioprecursors of the active compounds of the present invention.

For the purposes of this specification the term 'pharmaceutically acceptable bioprecursors' of an active compound of the invention means a compound having a structural formula different from the active compound but which nonetheless, upon administration to a warm-blooded animal is converted in the patient's body to the active compound.

EXAMPLE 39

N-hydroxy succinimid ester of N-[β-(4-hydroxy carbonylphenoxy)ethyl]-1-desoxynojirimycin

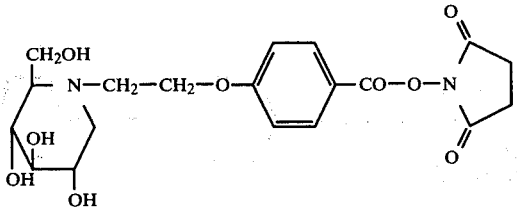

3,27 g of the compound of example 32 were dissolved in 35 ml hot dry DMF, cooled to about 25° C. and 1.3 g N-hydroxy succinimid and 2.3 g dicyclohexylcarbodiimid were added under stirring. The mixture was stirred for 20 hours, then the precipitated dicyclohexyl urea was filtered off and the filtrate was concentrated at 30° C. in a water bath. The residue was taken up with about 25 ml of warm water the undissolved residues were quickly filtered off and the filtrate was crystallized in a ice bath. 2.2 g of colourless crystals of a melting point of 137°–139° C. (decomp.).

EXAMPLE 40

N-[β-(4-carbamoyl-phenoxy)-ethyl]-1-desoxynojirimycin

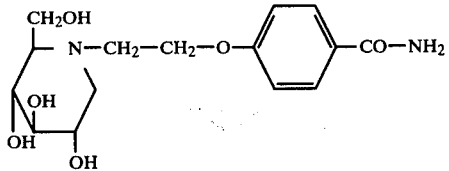

6 g of the compound of example 39 were added to 60 ml 25%ic ammonia and stirred for 24 hours. The mixture was then concentrated, taken up with little water and applied to a column of 120 cm length and 5 cm width such column having cellulose (Avicel Merck) as the solide phase and the mobile phase was aqueous acetone. The desired compound was obtained with 90 percent acetone. After recrystallization from a little water 2.6 g of colourless crystals of the melting point 183°-184° C. were obtained. Analogously were obtained:

EXAMPLE 41

N-[β-(4-morpholinocarbonyl-phenoxy)-ethyl]-1-desoxynojirimycin isolated as a foam.
Rf-value=0.595
Rf-value for 1-desoxynojirimycin=0.135
Running agent: chloroform/methanol/ammonia (25%) in a volume ratio of 6:4:1.
The Rf-values were determined in thin-layer chromatography of silicagel 60 F 254.

EXAMPLE 42

N[2-(4-phenylcarbamoylphenoxy)-ethyl]-1-desoxynojirimycin

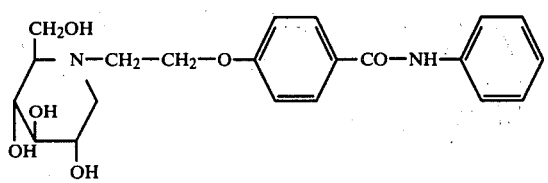

6 g of the compound of example 39 were stirred with 15 ml aniline at 120° C. bath temperature for 28 hours. The mixture was cooled and the precipitated residue was taken up with ethyl acetate filtered off and washed with ethyl acetate. The solid product was taken up with 30 ml 1 N sodium hydroxide filtered off and washed with water. After recrystallization from DMF/water 3.8 g of a slightly coloured product of a melting point of 196° C. were obtained.

EXAMPLE 43

N-[2-(4-phenylphenoxy)-ethyl]-1-desoxynojirimycin

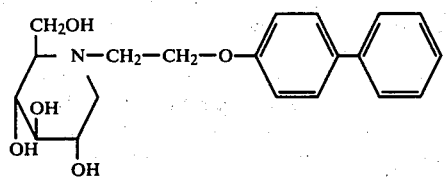

of a melting point of 198° C. was obtained analogously to example 1 from 1-desoxynorimiycin and 2-(4-phenylphenoxy)-ethyl bromide.

What is claimed is:

1. A 3,4,5-trihydroxypiperidine derivative of the formula

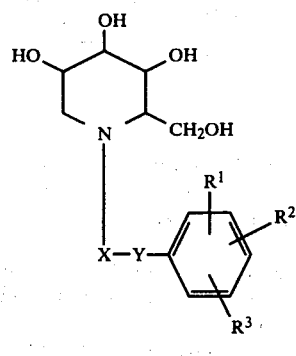

(I)

in which

X denotes a straight-chain or branched saturated or mono-ethylenically unsaturated hydrocarbon radical having 1 to 10 carbon atoms, Y denotes oxygen or sulphur and $R^1$, $R^2$ and $R^3$ are identical or different and independently of one another denote a hydrogen or halogen atom, an alkyl, monocylic or bi-cyclic carbocyclic aryl or aroxy, alkylthio, nitro, hydroxyl, cyano, amino, alkylamino, dialkylamino, amioalkyl, hydroxyalkyl, carboxylic or sulphonic acid acylamino, sulfonylamino, carboxylic or sulphonic acid acyloxy, carboxyl, carbalkoxy, alkylcarbonyl or formyl radical or a carboxamide or sulphonamide radical which is unsubstituted or substituted by $C_1$-$C_7$-alkyl or phenyl, each of said alkyl, alkoxy, alkylthio, alkylamino, aminoalkyl, hydroxyalkyl, carbalkoxy and alkylcarbonyl group having up to 12 carbon atoms; and each of said dialkylamino groups having up to 12 carbon atoms in each alkyl group.

2. A compound according to claim 1 in which X denotes a saturated or mono- ethylenically unsaturate alkyl radical with two to five carbon atoms.

3. A compound according to claim 1 or 2 in which $R^1$, $R^2$ and $R^3$ independently denote a hydrogen atom, a $C_1$-$C_8$-alkyl or alkoxy group, a halogen atom or a carboxyl, $C_1$-$C_8$-carbalkoxy, amino, carboxylic or sulphonic acid acylamino, carboxamide, mono-or bi-cyclic carboxylic aryl or amino-$C_1$-$C_8$-alkyl group.

4. A compund according to claim 1 or 2 in which $R^1$, $R^2$ and $R^3$ independently denote a hydrogen atom, a carboxyl, $C_1$-$C_8$-alkoxy, amino, carboxamide, carboxylic or sulphonic acid acylamino, mono- or bi-cyclic carboxylic aryl or an amino-$C_1$-$C_8$-alkyl group.

5. A compound according to claim 1 or 2 in which $R^1$, $R^2$ and $R^3$ independently denote a hydrogen atom, a $C_1$-$C_8$alkyl or alkoxy group or a halogen atom.

6. A compound according to claim 1 which is N-(5-phenoxypentyl)-1-desoxynojirimycin.

7. A compound according to claim 1 which is N-[4-(4-carbethoxyphenoxy)-buten-2-y1]-1-desoxynojirimycin.

8. A compound according to claim 1 which is N-[4tert.-butylphenylthio)-buten-2-y1]-1-desoxynojirimycin.

9. A compound according to claim 1 which is N-[β-(4-Ethoxycarbonyl-phenoxy)-ethyl]-1-desoxynojirimycin.

10. A compound according to claim 1 which is N-[β-(4-Hydroxycarbonylphenoxy)-ethyl]-1-desoxynojirimycin.

11. A compound according to claim 1 which is N-[4-(4-Phenylphenoxy)-buten-2y1]-1-desoxynojirimycin.

12. A medicament of claim 1 in the form of tablets, pills, dragees, capsules or ampoules.

13. A pharmaceutical composition containing as an active ingredient an amount effective for combating diabetes, hyperlipaemia, adiposity, arteriosclerosis or caries of a compound according to claim 1 in admixture with an inert pharmaceutical carrier.

14. A composition according to claim 13 containing from 0.1 to 99.5% by weight of the said active ingredient.

15. A medicament in dosage unit form containing as an active ingredient an amount effective for combating diabetes, hyperlipaemia, adiposity, arteriosclerosis or caries of a compound according to claim 1 in admixture with an inert pharmaceutical carrier.

16. A method for combating diabetes in warm-blooded animals which comprises administering to said animals an effective anti-diabetic amount of an active compound according to claim 1 either alone or in admixture with a diluent or in the form of a medicament.

17. A method for combating hyperlipaemia in warm-blooded animals which comprises administering to said animals an effective anti-hyperlipaemia amount of an active compound according to claim 1 either alone or in admixture with a diluent or in the form of a medicament.

18. A method for combating adiposity in warm-blooded animals which comprises administering to said animals an effective anti-adiposity amount of an active compound according to claim 1 either alone or in admixture with a diluent or in the form of a medicament.

19. A method for combating arteriosclerosis in warm-blooded animals which comprises administering to said animals an effective anti-arteriosclerosis amount of an active compound according to claim 1 either alone or in admixture with a diluent or in the form of a medicament.

20. A method for combating caries in warm-blooded animals which comprises administering to said animals an effective anti-caries amount of an active compound according to claim 1 either alone or in admixture with a diluent or in the form of a medicament.

21. A method according to claim 16 in which the active compound is administered in an amount of 1 to $1 \times 10^4$ saccharase inhibitor units per kg body weight per day.

22. A method according to claims 16 or 21 in which the active compound is administered orally.

23. A method according to claim 17 in which the active compound is administered in an amount of 1 to $1 \times 10^4$ saccharase inhibitor units per kg body weight per day.

24. A method according to claims 17 or 23 in which the active compound is administered orally.

25. A method according to claim 18 in which the active compound is administered in an amount of 1 to $1 \times 10^4$ saccharase inhibitor units per kg body weight per day.

26. A method according to claims 18 or 25 in which the active compound is administered orally.

27. A method according to claim 19 in which the active compound is administered in an amount of 1 to $1 \times 10^4$ saccharase inhibitor units per kg body weight per day.

28. A method according to claims 19 or 27 in which the active compound is administered orally.

29. A method according to claim 20 in which the active compound is administered in an amount of 1 to $1 \times 10^4$ saccharase inhibitor units per kg body weight per day.

30. A method according to claims 20 and 29 in which the active material is administered orally.

31. A medicated feed comprising an active compound in an amount effective for reducing fat deposition according to claim 1 in admixture with nutritious material.

* * * * *